United States Patent
Saville et al.

(10) Patent No.: US 7,312,056 B2
(45) Date of Patent: Dec. 25, 2007

(54) ENHANCEMENT OF ENZYME ACTIVITY THROUGH PURIFICATION AND IMMOBILIZATION

(75) Inventors: Bradley A. Saville, Toronto (CA); Mikhail I. Khavkine, Newmarket (CA)

(73) Assignee: Immortazyme Company, Ontario (CA)

( * ) Notice: Subject to any disclaimer, the term of this patent is extended or adjusted under 35 U.S.C. 154(b) by 607 days.

(21) Appl. No.: 10/797,020

(22) Filed: Mar. 11, 2004
(Under 37 CFR 1.47)

(65) Prior Publication Data
US 2006/0134766 A1 Jun. 22, 2006

(30) Foreign Application Priority Data
Mar. 13, 2003 (CA) ................................... 2421829

(51) Int. Cl.
| | | |
|---|---|---|
| C12N 11/14 | (2006.01) | |
| C12N 11/06 | (2006.01) | |
| C12N 9/96 | (2006.01) | |
| C12N 9/14 | (2006.01) | |
| C12N 9/26 | (2006.01) | |
| C12N 9/34 | (2006.01) | |

(52) U.S. Cl. ...................... 435/176; 435/181; 435/188; 435/195; 435/201; 435/205

(58) Field of Classification Search ..................... None
See application file for complete search history.

(56) References Cited

U.S. PATENT DOCUMENTS 4,369,226 A * 1/1983 Rembaum .................... 428/334
5,998,183 A   12/1999 Le Fevre et al.
6,582,606 B2  6/2003 Laustsen

OTHER PUBLICATIONS

Woodroof, Aubrey E., "Use of Glutaraldehyde and Formaldehyde to Process Tissue Heart Valves," Journal of Bioengineering, vol. 2, No. 1-2, 1978, pp. 1-10.
Walt, David R., "The Chemistry of Enzyme and Protein Immobilization With Glutaraldehyde," Trac. Trends in Analytical Chemistry, Cambridge, GB, vol. 13, No. 10, Nov. 1994, pp. 425-430.

* cited by examiner

Primary Examiner—Marianne P. Allen
(74) Attorney, Agent, or Firm—Jeffrey S. Melcher; Manelli Denison & Selter, PLLC

(57) ABSTRACT

An improved method of making an immobilized enzyme comprising (a) treating an immobilization support with an aqueous solution comprising a cross-linking agent and polymeric aldehyde species and active centre species to produce a modified support; (b) isolating the modified support; (c) treating an enzyme solution with the modified support to produce the immobilized enzyme, the improvement comprising treating the aqueous solution of cross-linking agent with an effective amount of a purifying agent to reduce the amount of the polymeric aldehyde species and active centre species. Alternatively, the invention provides an improved method of making an immobilized enzyme comprising (a) treating an immobilization support with an aqueous enzyme solution to produce an adsorbed immobilized enzyme; (b) isolating the adsorbed immobilized enzyme; and treating the adsorbed immobilized enzyme with an effective amount of an aqueous solution comprising a cross-linking agent and polymeric aldehyde species and active centre species to produce the immobilized enzyme, the improvement comprising treating the cross-linking agent with an effective amount of a purifying agent, to reduce the amount of the polymeric species and active centre species. Preferably, the cross-linking agent is glutardaldehyde, the purifying agent is activated carbon, the immobilization agent is a silica gel, zeolite or activated carbon, and the enzyme is amylase.

8 Claims, 2 Drawing Sheets

ENHANCEMENT OF ENZYME ACTIVITY THROUGH PURIFICATION AND IMMOBILIZATION

FIELD OF THE INVENTION

This invention relates to the use of enzymes for industrial processes, particularly, use of immobilized enzymes on a matrix used in chemical processes, and purification methods advantageous for the enhancement of enzyme activity and stability

BACKGROUND OF THE INVENTION

The industrial use of enzymes is often limited by their high cost and rapid inactivation. Soluble enzymes are lost with the product at the conclusion of a process, and must be replenished. One area of technological development involves modification of proteins to enhance their activity and/or stability. Processes, such as those involving site-directed mutagenesis and the cultivation of wild forms of enzymes in extreme environments, i.e., extremophiles, have led to significant advances in enzyme technology involving the reduction in the cost per unit of enzyme activity.

Another means to improve the economic feasibility of enzymes for industrial processes is through enzyme immobilization onto a matrix, which may facilitate re-use of the enzyme. Immobilization research has focused upon means to enhance the transfer of enzymes onto the support, and upon means to ensure that the immobilized enzymes remain active. Inactivation of enzymes during catalytic turnover is, however, a key obstacle which may limit the economic feasibility of enzyme-mediated processes. Enzymes may be inactivated by extremes of temperature, pH, shear, and also by free radicals and other reactive species present in the reaction medium. Immobilization technology has the potential to reduce such enzyme inactivation, and, thus, extend the enzyme's useful lifespan.

The development of an immobilized enzyme requires a choice of support matrix and a choice of enzyme immobilization method. These choices may have a dramatic impact on the quantity of enzyme transferred to the support, along with the activity and stability of the attached enzyme.

Activated charcoal is a well-known absorbent, and has been previously used for enzyme immobilization via absorption (A. S. Rani, M. L. M. Das, S. Satyanarayana, J. Mol. Catal. B. Enzymatic, 10, 471, 2000; W. Hassler, Purification with Activated Carbon, Chemical Publishing Co., New York, 1974), and following derivatization. Le Fevre and Saville, U.S. Pat. No. 5,998,183, describes the use of siliceous materials for enzyme immobilization.

Glutaraldehyde is a well-known protein cross-linking agent, used for enzyme immobilization and for fixation of samples for scanning electron microscopy (D. R. Walt and V. I. Agayn, Trends Anal. Chem., 13(10), 425, 1994). Its propensity to cause protein denaturation is well known. Typically, highly purified forms of glutaraldehyde are used for electron microscopy, whereas standard commercial grades of glutaraldehyde are typically used for immobilization. These commercial grades may include, in addition to the pure aldehyde, polymers of glutaraldehyde, cyclic structures, and acetals. A recent review (Walt and Agayn ibid) reached no clear consensus on the benefits/disadvantages of any of the forms of glutaraldehyde used for immobilization.

U.S. Pat. No. 4,438,196—Oreste J. Lantero Jr. is an example of derivation and describes immobilization onto activated carbon after the support has been derivatized using a polyamine compound or a copolymer of a polyamine and an epihalohydrin.

SUMMARY OF THE INVENTION

It is an object of the present invention to produce an enzyme form of superior activity and stability for use in industrial processes. Such an improved enzyme form may be produced by immobilization, reagent purification, or a combination thereof.

One aspect of the process according to the present invention uses an immobilization technique known as cross-linking, using two well-known supports for conventional catalysis, namely, activated carbon and siliceous materials, such as; for example, zeolites and silica gel.

In a further aspect, we have discovered that (a) purification of, for example, glutaraldehyde for use as a cross-linking agent prior to use for immobilization can substantially improve the stability of enzymes attached onto supports, and, (b), that activated charcoal, when used in combination with glutaraldehyde as a cross-linking agent, acts as an excellent support matrix for immobilization of enzymes.

We have found that purification of the glutaraldehyde cross-linking agent to remove polymeric forms and other active centres species can substantially affect the stability of the immobilized enzyme.

By the term "active centre species" in this specification is meant compounds that facilitate the formation of polymeric forms of the cross-linking aldehydes of use in the practice of the invention. As hereinafter described, surprisingly, although it is apparent that the presence of polymeric forms of, for example, glutaraldehyde, affects enzyme stability, it is also apparent that the removal of polymeric aldehyde forms alone is not sufficient.

Accordingly, the invention provides in one aspect, an improved method of making an immobilized enzyme comprising (a) treating an immobilization support with an aqueous solution comprising a cross-linking agent and polymeric aldehyde species and active centre species to produce a modified support; (b) isolating said modified support; (c) treating an enzyme solution with said modified support to produce said immobilized enzyme, the improvement comprising treating said aqueous solution of cross-linking agent with an effective amount of a purifying agent to reduce the amount of said polymeric aldehyde species and active centre species.

In a further aspect the invention provides an improved method of making an immobilized enzyme comprising (a) treating an immobilization support with an aqueous enzyme solution to produce an adsorbed immobilized enzyme; (b) isolating said adsorbed immobilized enzyme; and treating said adsorbed immobilized enzyme with an effective amount of an aqueous solution comprising a cross-linking agent and polymeric aldehyde species and active centre species to produce said immobilized enzyme, the improvement comprising treating said cross-linking agent with an effective amount of a purifying agent, to reduce the amount of said polymeric aldehyde species and active centre species.

Preferably, but not exclusively, the aqueous solution of the cross-linking agent is pre-treated with the purifying agent, and separated therefrom prior to mixing with the immobilization support. The purifying agent, for example, an activated carbon, is believed to selectively adsorb polymeric aldehyde species and active centre species, particularly, in the case of glutaraldehyde.

The invention is of particular utility with enzymes selected from the group consisting of amylase, glucoamylase, cellulase, xylanase, glucose isomerase, or any other group 3 hydrolase.

Immobilization supports may be selected, for example only, from a method as hereinabove defined wherein said cross-linking agent is glutaraldehyde.

BRIEF DESCRIPTION OF THE DRAWINGS

In order that the invention may be better understood, preferred embodiments will now be described by way of example only, wherein.

DETAILED DESCRIPTION OF PREFERRED EMBODIMENTS

The invention is illustrated by the following examples.

EXAMPLE 1

Immobilization with Electron-Microscopy Grade Glutaraldehyde (EMG)

Figure 1:
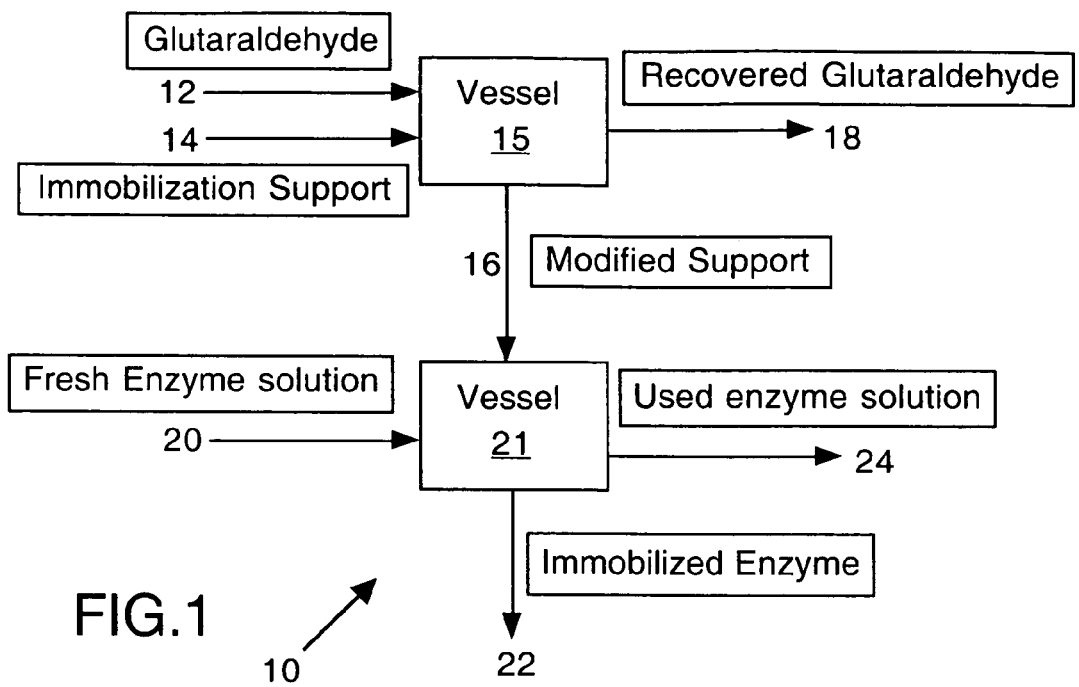
FIGS. 1, 2 and 3 represent schematic outlines of preparing immobilized enzymes using various grades of glutaraldehyde according to the prior art and the present invention; and wherein the same numerals denote analogous reagents and steps.

An immobilized enzyme was prepared by the process shown generally as (10) in FIG. 1.

4% solution of glutaraldehyde (GA) (12) was prepared by dilution from 25 w/v % electron microscopy grade glutaraldehyde. Spectroscopic analysis showed that the 4% solution contained about 94% monomeric GA.

Silica gel (40 g) (14), as an immobilization support, was added to 250 mL of 4% GA solution and mixed in vessel (15) for 3 h at room temperature, with gentle stirring to keep the silica gel suspended. The modified silica gel (16) was recovered by vacuum filtration, then dried overnight in a fumehood and for 2 h at 50° C. in a vacuum oven. The filtrate (recovered glutaraldehyde) (18) was assayed for monomeric and polymeric GA whereby it was found that the concentration of polymeric GA had increased by more than a factor of 20, now comprising about 60% of the forms of glutaraldehyde in the solution.

The modified silica gel (20 g) (16) was suspended in 250 mL of fresh amylase solution (20) which was prepared by diluting 25 mL of raw amylase with 225 mL of pH 6 phosphate buffer, for 4 h, with gentle stirring in vessel (21). The resulting immobilized enzyme (22) was recovered from the enzyme solution (24) by vacuum filtration. Three sequential assays of immobilized enzyme activity were conducted, to determine the initial activity and the activity retained after the $1^{st}$ and $2^{nd}$ uses of the enzyme for hydrolysis of corn starch. The results are presented in Table 1.

EXAMPLE 2

Immobilization with Commercial Grade Glutaraldehyde) (ASIS)

An immobilized enzyme was prepared according to the process as described in Example 1, with reference to FIG. 1 in an analogous manner.

4% solution of glutaraldehyde (GA) (12) was prepared by dilution from 50 w/v % commercial grade glutaraldehyde. Spectroscopic analysis showed that the 4% solution contained approximately 91% monomeric GA.

Silica gel (40 g) (14) added to 250 mL of 4% GA solution (12) and mixed in vessel (15) for 3 h at room temperature, with gentle stirring to keep the silica gel suspended. The modified silica gel (16) was recovered by vacuum filtration, then dried overnight in a fumehood and for 2 h at 50° C. in a vacuum oven. The recovered glutaraldehyde (18) filtrate was assayed for monomeric and polymeric GA whereby it was found that the concentration of polymeric GA had increased by about a factor of 15, now making up about 56% of the total forms of glutaraldehyde in the GA solution (18).

The modified silica gel (20 g) (16) was suspended in 250 mL of fresh amylase solution (20), which was prepared by diluting 25 mL of raw amylase with 225 mL of pH 6 phosphate buffer, for 4 h in vessel (21), with gentle stirring. The resulting immobilized enzyme (22) was recovered from the enzyme solution (24) by vacuum filtration. Three sequential assays of immobilized enzyme activity were conducted, to determine the initial activity and the activity retained after the $1^{st}$ and $2^{nd}$ uses of the enzyme for hydrolysis of corn starch. The results are presented in Table 1.

EXAMPLE 3

Immobilization with Purified Commercial Grade Glutarladehyde (PUR(S))

Figure 2:
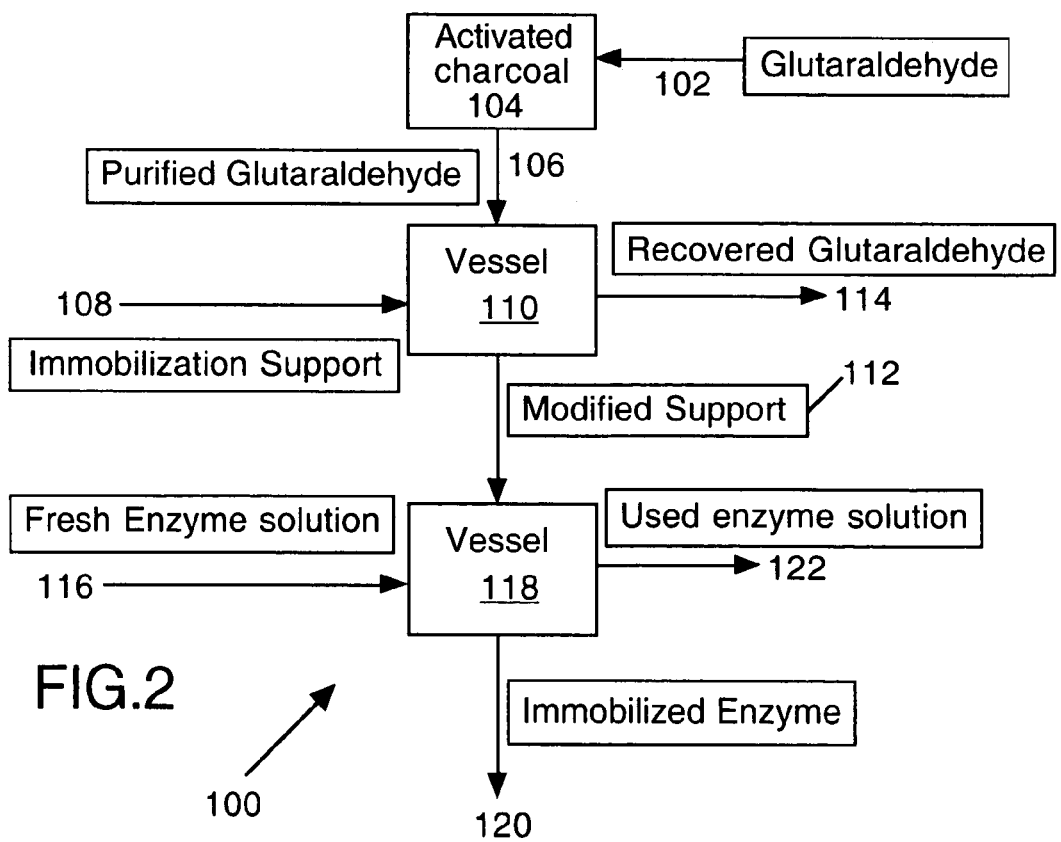

An immobilized enzyme was prepared by the process shown generally as (100) in FIG. 2.

4% solution of glutaraldehyde (GA) (102) was prepared by dilution from 50 w/v % commercial grade glutaraldehyde. The GA solution was then purified by incubation with 3.6% (w/v) Darco G60™ (activated charcoal) (104) in vessel (104) for 0.5-12 hours, and then recovered by filtration. Spectroscopic analysis showed that the 4% purified gluaraldehyde solution (106) contained mainly monomeric GA at about 93% of the total.

Silica gel (40 g) (108) as an immobilization support was added to 250 mL of 4% purified GA solution (106) in vessel 110 and mixed for 3 h at room temperature, with gentle stirring to keep the silica gel suspended. The modified silica gel (112) was recovered by vacuum filtration, dried overnight in a fumehood, and then dried for 2 h at 50° C. in a vacuum oven. The recovered glutaraldehyde filtrate (114) was assayed for monomeric and polymeric GA, whereby it was found that the concentration of polymeric GA had increased by about a factor of 3, now comprising about 20% of the total forms of glutaradehyde in the GA solution (114).

The modified silica gel (20 g) (112) was suspended in 250 mL of fresh amylase solution prepared by diluting 25 mL of raw amylase with 225 mL of pH 6 phosphate buffer in vessel (118) for 4 h, with gentle stirring. The resulting immobilized enzyme (120) was recovered from the enzyme solution (122) by vacuum filtration. Three sequential assays of immobilized enzyme (120) activity were conducted, to determine the initial activity and the activity retained after the $1^{st}$ and $2^{nd}$ uses of the enzyme for hydrolysis of corn starch. The results are presented in Table 1.

TABLE 1

Effect of GA Quality and Purification on Amylase Immobilization

| GA Treatment | Amylase Units/g | % Retained Activity |
| --- | --- | --- |
| EMG (Example 1) | | |
| $1^{st}$ use | 57 | 100 |
| $2^{nd}$ use | 45 | 79 |
| $3^{rd}$ use | 34 | 60 |

TABLE 1-continued

Effect of GA Quality and Purification on Amylase Immobilization

| GA Treatment | Amylase Units/g | % Retained Activity |
|---|---|---|
| ASIS (Example 2) | | |
| 1st use | 91 | 100 |
| 2nd use | 34 | 37 |
| 3rd use | 23 | 25 |
| PUR (S) (Example 3) | | |
| 1st use | 57 | 100 |
| 2nd use | 57 | 100 |
| 3rd use | 57 | 100 |

It can be clearly seen that the purity of glutaraldehyde clearly has an impact on the efficacy of the immobilized enzyme. All three forms initially contain mainly monomeric GA, but the commercial form (ASIS) likely also has some acetals. Of the three formulations, the commercial form also has the most polymeric GA at the beginning of the immobilization process. The polymeric GA content increased substantially during immobilization with each of the commercial and electron-microscopy grades of GA. However, the polymer content of the GA solution that had been purified with Darco G60™ activated carbon, PUR(S), increased much less during immobilization. These differences had a significant impact on enzyme immobilization efficacy in subsequent enzymatic reactions.

The commercial grade of unpurified GA (ASIS) gave the greatest initial enzyme activity (Example 2), but also the greatest rate of enzyme deactivation. This is possibly due to desorption from the support. The EM grade and the purified GA (PUR(S)) provided comparable initial enzyme activities, albeit less than the commercial grade (ASIS). However, most notably, the immobilized enzyme produced using purified GA (PUR(S)) with activated carbon (Example 3) was stable through three uses. This is in contrast to the immobilized enzyme produced using the EM purified grade (EMG), which decreased by about 20% per use. This difference in stability is likely linked to the quantity of polymeric GA in solution, and the removal of active centres that are believed to catalyse reformation of polymeric species during immobilization.

EXAMPLE 4

Simultaneous Support Modification and Glutaraldehyde Purification

An immobilized enzyme was prepared according to an analogous process to FIG. 1.

4% solution of glutaraldehyde (GA) (12) was prepared by dilution of 50 w/v % commercial grade glutaraldehyde in pH 4 buffer. Silica gel (40 g) (14), as an immobilization support and activated carbon (25 g) (14) as a purifier, were simultaneously suspended in 250 mL of 4% GA solution in vessel (15) for 3 h at room temperature, with gentle stirring to keep the solids suspended. The modified silica gel (16) and activated carbon (16) were separately recovered by vacuum filtration, dried overnight in a fumehood, and then dried for 2 h at 50° C. in a vacuum oven.

Modified silica gel (20 g) (16) was added to 250 mL of amylase solution (20) prepared by diluting 25 mL of raw amylase with 225 mL of pH 5 phosphate buffer in vessel (21) and mixed for 4 h, with gentle stirring to keep the silica gel (16) suspended. The resulting immobilized enzyme (22) was separated from the enzyme solution by vacuum filtration. Four sequential assays of immobilized enzyme activity were conducted, to determine the initial activity and the activity retained after the $1^{st}$, $2^{nd}$, and $3^{rd}$ uses of the enzyme (22) for hydrolysis of corn starch. The results are presented in Table 2.

EXAMPLE 5

Immobilization to Activated Carbon

Figure 3:
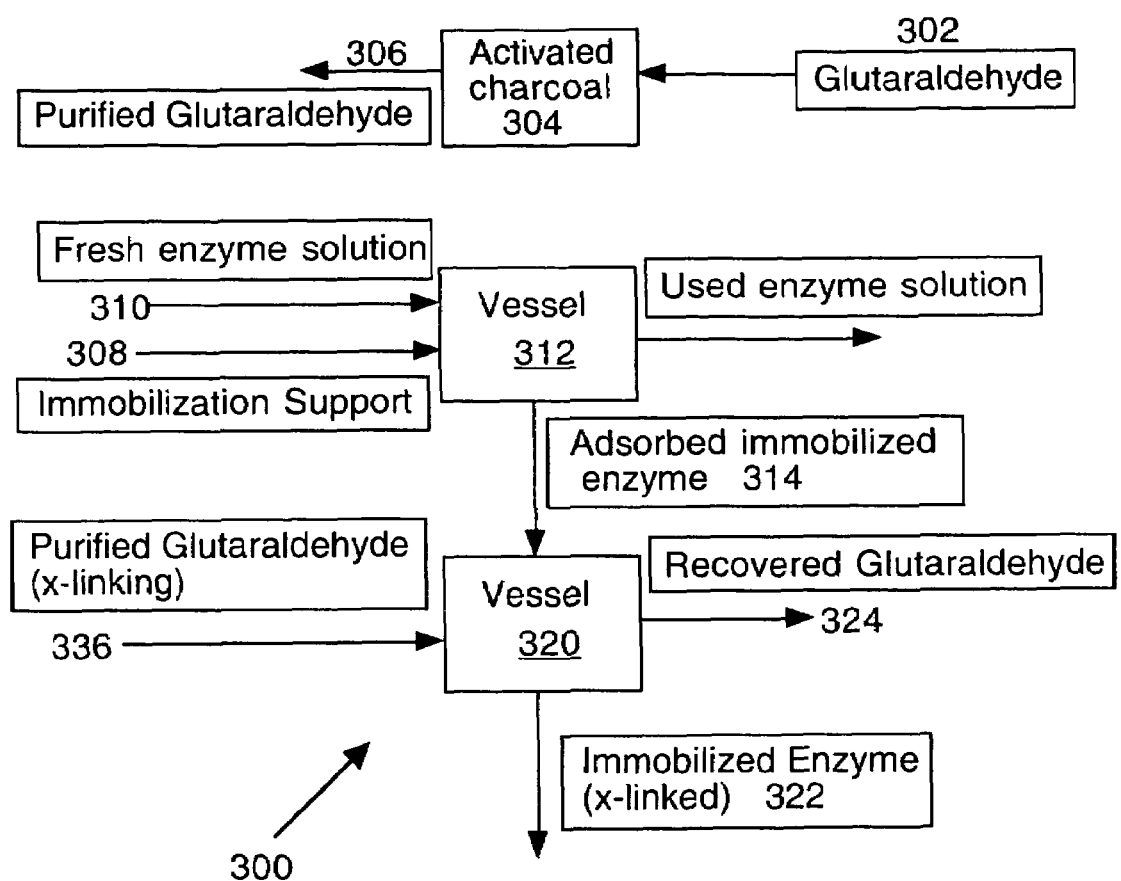

An immobilized enzyme was prepared by a process shown generally as 300 in FIG. 3.

4% solution of glutaraldehyde (GA) (302) was prepared by dilution of 50 w/v % commercial grade glutaraldehyde in pH 4 buffer. The GA solution (302) was purified by mixing with 4.0% (w/v) activated carbon (304) for 0.75 h, and then recovered by filtration (306).

50 g of fresh activated carbon as an immobilization support (308) was suspended in 255 mL of fresh amylase solution (30 mL raw Allzyme+225 mL 0.05 M phosphate buffer, pH 5.2) (310) in vessel (312) for 3 h, with gentle stirring. The adsorbed immobilized enzyme (314) was recovered by vacuum filtration, and then suspended, with gentle stirring, in 250 mL of 4% purified GA cross-linking solution (306) in vessel (320) for 30 min at room temperature to crosslink adsorbed enzyme (314). The cross-linked immobilized enzyme (322) was recovered by vacuum filtration from recovered glutaraldehyde (324), and then washed with 300 mL of water. The immobilized enzyme (322) was dried overnight in a fumehood, and then dried for 1 h at 50° C. in a vacuum oven. Four sequential assays of immobilized enzyme activity were conducted, to determine the initial activity and the activity retained after the $1^{st}$, $2^{nd}$, and $3^{rd}$ uses of the enzyme for hydrolysis of corn starch. The results are presented in Table 2.

TABLE 2

Use of Purified Glutaraldehyde for Immobilization on Silica Gel and Activated Carbon

| Immobilized Enzyme Form | Amylase Units/g | % Retained Activity |
|---|---|---|
| SGel/AC* (Example 4) | | |
| 1st use | 32 | 100 |
| 2nd use | 32 | 100 |
| 3rd use | 30 | 94 |
| 4th use | 28 | 88 |
| AC* (Example 5) | | |
| 1st use | 26 | 100 |
| 2nd use | 17 | 65 |
| 3rd use | 20 | 77 |
| 4th use | 18 | 69 |

Table 2 shows that the use of purified GA with activated carbon as a purifier has produced, in each example, an immobilized enzyme that shows very good retention of activity on multiple uses. Further, the use of silica gel provides better performance than the use of activated carbon as an immobilization support.

EXAMPLE 6

Immobilization of Cellulase onto Silica Gel

4% solution of glutaraldehyde (GA) (102) was prepared by dilution from 50 w/v % commercial grade glutaraldehyde. The GA solution was then purified by incubation with 3.6% (w/v) activated charcoal (104) in vessel (104) for 0.5-12 hours, and then recovered by filtration. Spectroscopic analysis showed that the 4% purified gluaraldehyde solution (106) contained mainly monomeric GA at about 70 to 76% of the total.

Silica gel (10 g) (108) as an immobilization support was added to 250 mL of 4% purified GA solution (106) in vessel 110 and mixed for 3 to 8 h at room temperature, with gentle stirring to keep the silica gel suspended. The modified silica gel (112) was recovered by vacuum filtration.

The modified silica gel (10 g) (112) was suspended for 4 to 48 h in 250 mL of fresh cellulase solution, prepared by diluting raw cellulase with pH 4.8 citrate buffer in vessel (118), with gentle stirring. The resulting immobilized enzyme (120) was recovered from the enzyme solution (122) by vacuum filtration. Four sequential assays of immobilized enzyme (120) activity were conducted, with wash steps to replicate enzyme exposure to reaction conditions, to determine the initial activity and the activity retained after the $1^{st}$, $2^{nd}$, and $3^{rd}$ uses of the enzyme for hydrolysis. The immobilized enzyme retained 43% of its original activity after the first use, with a further 10% loss of activity on each subsequent use. By comparison, without the glutaraldehyde purification step, 95% of the original activity was lost after the first use of the immobilized enzyme.

As mentioned hereinabove, although it is apparent that the presence of polymeric forms of, for example, glutaraldehyde affects enzyme stability, it is also apparent that the removal of polymeric aldehyde forms alone is not sufficient. The electron microscopy grade of glutaraldehyde possessed the least amount of polymeric forms at the beginning of immobilization, and the commercial grade contained the most polymeric GA. However, by the end of the immobilization, the quantity of polymeric GA had increased substantially in both the commercial and electron-microscopy grade GA solutions, but had, by comparison, increased only marginally in the GA solution purified with activated carbon.

As shown in Table 1, higher initial concentrations of polymeric GA present in the commercial grade of glutaraldehyde translated into higher activity of the immobilized enzyme. However, the greatest stability was inversely correlated with the FINAL concentration of polymeric GA in the immobilization solution. The ability of activated carbon to limit/prevent GA polymer formation appears therefore critical. It is also apparent that activated carbon removes some "active centres species" that, in some fashion, facilitate formation of polymeric forms of glutaraldehyde, since the final quantity of polymeric GA in the solution was not directly correlated with the initial quantity of polymeric GA in the solution.

Although this disclosure has described and illustrated certain preferred embodiments of the invention, it is to be understood that the invention is not restricted to those particular embodiments. Rather, the invention includes all embodiments which are functional or mechanical equivalents of the specific embodiments and features that have been described and illustrated.

The invention claimed is:

1. An improved method of making an immobilized enzyme comprising:
    (a) treating an aqueous solution comprising glutaraldehyde polymeric glutaraldehyde, cyclic structures and acetals with an effective amount of a purifying agent to reduce the amount of said polymeric glutaraldehyde cyclic structures and acetals, and produce a purified glutaraldehyde cross-linking agent solution;
    (b) treating an immobilization support with said purified glutaraldehyde solution to produce a modified support;
    (c) isolating said modified support; and
    (d) treating an enzyme solution with said modified support to produce said immobilized enzyme.

2. A method as defined in claim 1 wherein said immobilization support is selected from the group consisting of a natural or synthetic activated carbon material and a siliceous material selected from natural or synthetic zeolites, natural or synthetic sodium aluminosilicate, amorphous aluminosilicate and silica gel.

3. A method as defined in claim 1 wherein said purifying agent is an activated carbon.

4. A method as defined in claim 1 wherein said enzyme is an enzyme selected from the group consisting of amylase, glucoamylase, cellulase, xylanase, glucose isomerase, or any other group 3 hydrolase.

5. An improved method of making an immobilized enzyme comprising:
    (a) treating an immobilization support with an aqueous enzyme solution to produce an adsorbed immobilized enzyme;
    (b) isolating said adsorbed immobilized enzyme;
    (c) treating an aqueous solution comprising glutaraldehyde, polymeric glutaraldehyde cyclic structures and acetals with an effective amount of a purifying agent to reduce the amount of said polymeric glutaraldehyde cyclic structures and acetals, and produce a purified glutaraldehyde cross-linking agent solution; and
    (d) treating said adsorbed immobilized enzyme with said purified glutaraldehyde cross-linking solution to produce said immobilized enzyme product.

6. A method as defined in claim 5 wherein said immobilization support is selected from the group consisting of a natural or synthetic activated carbon material and a siliceous material selected from natural or synthetic zeolites, natural or synthetic sodium aluminosilicate, amorphous aluminosilicate and silica gel.

7. A method as defined in claim 5 wherein said purifying agent is an activated carbon.

8. A method as defined in claim 5 wherein said enzyme is an enzyme selected from the group consisting of amylase, glucoamylase, cellulase, xylanase, glucose isomerase, or any other group 3 hydrolase.

* * * * *